United States Patent [19]

Stuart

[11] Patent Number: 4,680,028
[45] Date of Patent: Jul. 14, 1987

[54] FLEXIBLE BREAST RECEPTOR FOR BREAST PUMP

[75] Inventor: Herbert H. Stuart, Nashville, Tenn.
[73] Assignee: Lact-Assist, Incorporated, Nashville, Tenn.
[21] Appl. No.: 626,968
[22] Filed: Jul. 2, 1984
[51] Int. Cl.[4] .............................................. A61M 1/06
[52] U.S. Cl. ........................................ 604/74; 604/75; 604/316
[58] Field of Search ............ 128/DIG. 21; 119/14.31, 119/14.47–14.52; D24/14, 23, 24, 47, 51, 55; 604/74–76, 316, 212

[56] References Cited

U.S. PATENT DOCUMENTS

| 301,535 | 7/1884 | Tatum . | |
|---|---|---|---|
| 3,289,634 | 12/1966 | Simons | 119/14.52 |
| 3,683,424 | 8/1972 | Pangman | 128/DIG. 21 |
| 3,911,920 | 10/1975 | Susinn | 604/75 |
| 4,263,912 | 4/1981 | Adams | 604/75 |

FOREIGN PATENT DOCUMENTS 968660  6/1975  Canada .................................. 604/74

Primary Examiner—Stephen C. Pellegrino
Assistant Examiner—J. L. Kruter
Attorney, Agent, or Firm—Harrington A. Lackey

[57] ABSTRACT

A breast receptor for a breast pump having means for creating a vacuum within the breast receptor in which the wall thicknesses of the flexed portions of the receptor engaging the nipple and areola are reduced in order to produce optimum lactating conditions, including optimum responsiveness to the external touch stimulus, and which will most nearly simulate the mouth of a suckling infant.

9 Claims, 2 Drawing Figures

U.S. Patent    Jul. 14, 1987    4,680,028
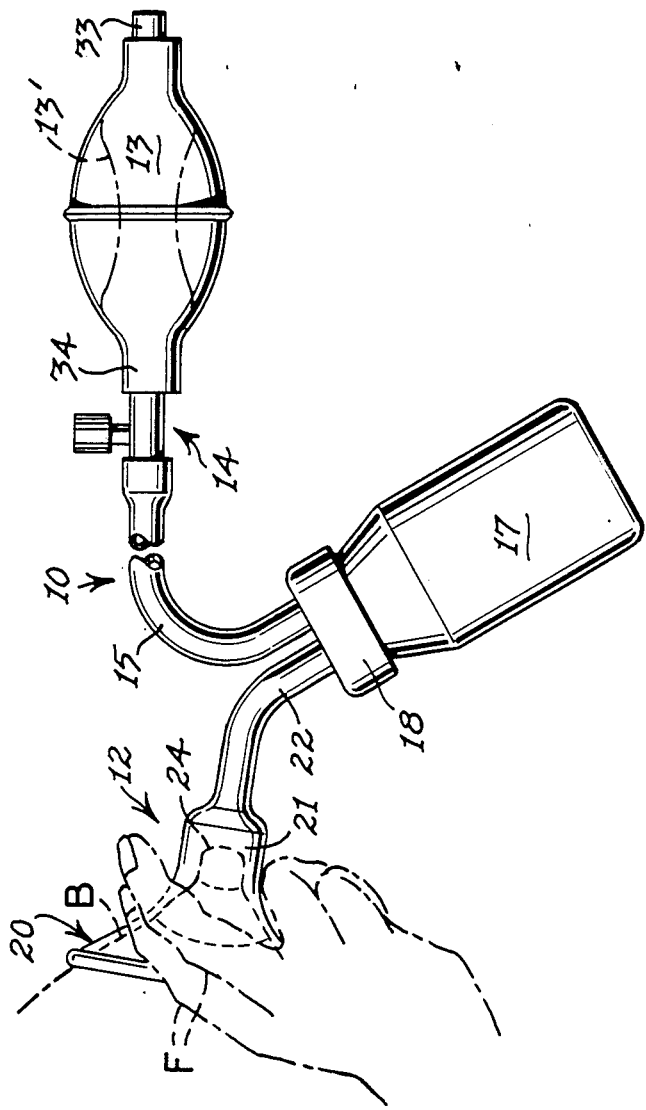
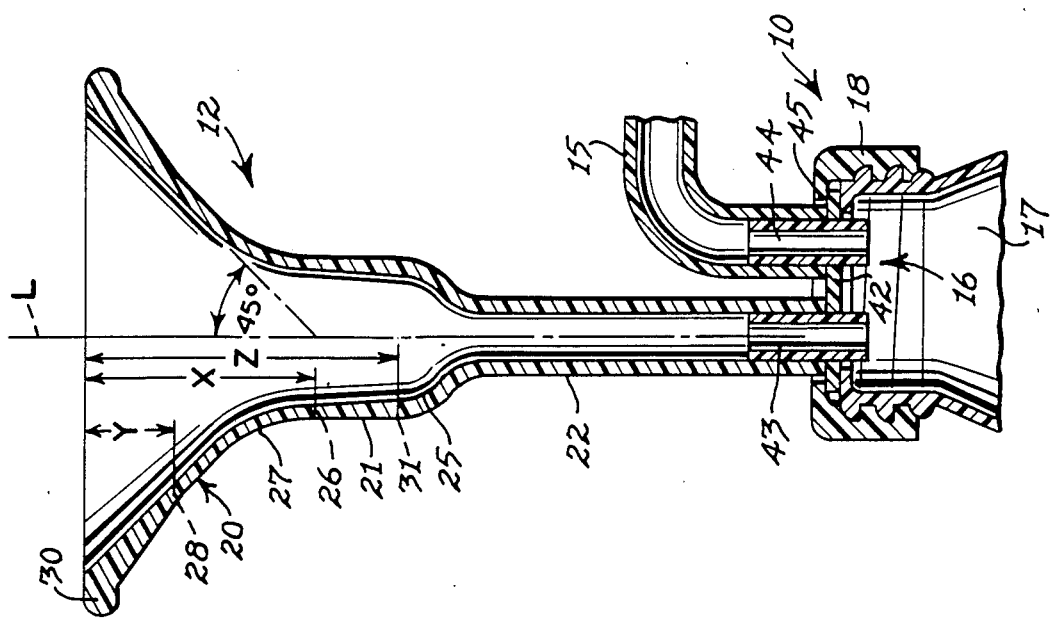

FLEXIBLE BREAST RECEPTOR FOR BREAST PUMP

BACKGROUND OF THE INVENTION

This invention relates to a breast pump, and more particularly to a breast receptor which will simulate the mouth of a suckling infant.

Breast pumps having breast receptors of various constructions are well known in the art, such as those disclosed in the following U.S. Pat. Nos.:

| | | |
|---|---|---|
| 316,584 | Turner | Apr. 28, 1885 |
| 1,156,202 | Barrett | Oct. 12, 1915 |
| 1,670,610 | Colby | May 22, 1928 |
| 1,847,656 | Lasker | Mar. 1, 1932 |
| 2,060,063 | Frimand | Nov. 10, 1936 |
| 2,222,811 | Dinesen | Nov. 26, 1940 |
| 3,738,363 | Lunas et al | Jun. 12, 1973 |
| 3,782,385 | Loyd | Jan. 1, 1974 |
| 3,822,703 | Davisson | Jul. 9, 1974 |
| 3,911,920 | Susinn | Oct. 14, 1975 |
| 4,263,912 | Adams | Apr. 28, 1981 |

Of the above patents, the following U.S. patents disclose breast receptors of plastic or elastic material:

| | | |
|---|---|---|
| 3,738,363 | Lunas et al | Jun. 12, 1973 |
| 3,782,385 | Loyd | Jan. 1, 1974 |
| 3,822,703 | Davisson | Jul. 9, 1974 |
| 3,911,920 | Susinn | Oct. 14, 1975 |
| 4,263,912 | Adams | Apr. 28, 1981 |

Although the above Adams U.S. Pat. No. 4,263,912, teaches variations in wall thickness (13, 15) in a breast receptor 12, nevertheless, the walls of the Adams breast receptor are thinner toward the outer flared end portion of the receptacle in order to simulate a peristaltic pumping action upon the breast.

None of the above patents disclose a breast pump incorporating a breast receptor in which the merging portions of the frusto-conical walls of the skirt and the wall of the tubular stem are relatively thin compared with the remaining wall portions of the receptor to increase the flexibility of these merging wall portions for the maximum suckling effect in response to the pumping action, and for optimum transfer of the touch stimulus from the hand of the mother to her breast through the wall of the receptor.

SUMMARY OF THE INVENTION

It is therefore an object of this invention to provide a breast receptor which is capable of very nearly simulating the "suckling effect" of an infant.

Another object of this invention is to provide a breast pump having a breast receptor, which not only is transparent and may be autoclaved, but also is capable of massaging the breast in response to the negative pressures produced in the receptor.

Another object of this invention is to provide in a breast pump, a breast receptor having a thin wall area engaging the nipple and the areola when the breast is received in the receptor to maximize the transfer of the touch stimulus from the fingers of the mother through the wall to her breast.

A further object of this invention is to provide in a breast pump, a breast receptor having variations in its wall thickness such that the portions of the stem and skirt, which are in engagement with the nipple, areola and adjoining breast portions, are very thin, the outer rim of the skirt is substantially thick for establishing a vacuum seal against the breast received within the receptor, and the tubular conduit and adjacent portion of the stem have relatively thick walls to prevent collapsing under negative pressures created by the pumping action to permit free flow of the milk from the receptor to a milk receptacle.

In a preferred form of the breast pump, the breast receptor is made of transparent, flexible, homogeneous material which may be autoclaved, and more specifically a thermo-setting silicone rubber.

BRIEF DESCRIPTION OF THE DRAWINGS

FIG. 1 is a side elevational view of a breast pump, including a breast receptor made in accordance with this invention receiving the human breast in a lactating position; and FIG. 2 is an enlarged fragmentary, sectional elevation of the breast receptor and a portion of the milk receptacle disclosed in FIG. 1.

DESCRIPTION OF THE PREFERRED EMBODIMENTS

Referring now to the drawings in more detail, the breast pump 10, disclosed in FIGS. 1 and 2, includes a breast receptor 12, made in accordance with this invention, a bulb or bulb pump 13, a control valve member 14, a flexible suction tube or conduit 15, a bottle coupling device 16 for connecting the receptor 12 and the suction line 15 to a conventional milk receptacle, such as a baby bottle 17, and a baby bottle cap 18. Except for the unique construction of the breast receptor 12, the remaining elements of the breast pump 10 are essentially disclosed in the prior application of Herbert H. Stuart and Kathy S. Smith, Ser. No. 437,347 for a "BREAST PUMP".

The breast receptor 12 includes the frusto-conical or flared skirt 20 of flexible material having its large end open for receiving a human breast B (FIG. 1) in a lactating position. The smaller end of the skirt 20 is also open and is in fluid communication with one end of a tubular stem 21, which is integrally formed with the skirt 20 of the same flexible material. The other end of the tubular stem 21 is reduced in size, but opens into one end of the receptor tube or conduit 22. The opposite end of the receptor tube 22 is also open. As disclosed in the drawings, the receptor tube 22 is also formed integrally with, and of the same flexible material as, the stem 21 and the skirt 20.

The degree of flare of the conical skirt 20 is such that it will be comfortable and substantially engaging most of the surface of the portion of the breast B received in its lactating position within the skirt 20. In order to render the skirt 20 comfortable to the breast B and also to accommodate breasts of varying sizes, the skirt 20 preferably has a flared or tapering wall of approximately 40°–50° to the longitudinal axis L of the skirt 20, and more specifically at approximately 45° angle to the longitudinal axis L. If the flare angle is substantially greater than 50°, the seal between the skirt 20 and the breast B will become ineffective in maintaining the vacuum within the receptor 20. If the flare angle is substantially less than 40°, only smaller size breasts B may be comfortably received within the skirt 20. Moreover, in many instances, the breast B will not be received deeply enough within the receptor 12 for the optimum suckling effect and lactating actions to be described. When properly seated within the receptor 12, the nipple 24 of the breast B is adapted to extend into the stem 21 as illustrated in FIG. 1.

The receptor tube 22 is preferably cylindrical and has a uniform wall thickness substantially throughout its length, which is great enough to prevent the tube 22 from collapsing under a reduction of internal air pressure when a vacuum is created by the actuation of the pump bulb 13. The wall thickness of the tube 22 is also great enough to provide stability and sealing engagement with the bottle coupling device 16, in order to provide free fluid communication between the interior of the tube 22 and the interior of the bottle or receptacle 17.

The other end portion (the upper end portion disclosed in FIG. 2) of the receptor tube 22 gradually enlarges and merges into the lower end portion of the substantially cylindrical stem 21. The wall thickness of the merging transition area 25 between the tube 22 and the stem 21 may be substantially the same or slightly greater than the wall thickness of the receptor tube 22.

The wall thickness of the stem 21 then gradually decreases from the transition area 25 to a point 26 (FIG. 2) which is substantially the terminal end portion of the cylindrical stem 21. From the terminal end portion 26, the wall of the receptor 12 flares outwardly to form the transition portion 27 between the stem 21 and the smaller end portion of the skirt 20. The wall thickness of the transition portion 27 is substantially uniform from the terminal end portion 26 to a point 28 located more than midway between the end portion 26 and the outer annular rim 30 defining the large open end of the skirt 20. The axial distance between the annular rim 30 and the terminal end portion 26 is represented by the distance X(FIG. 2); while the axial distance between the annular rim 30 and the terminal end portion 28 of the uniform wall thickness of the skirt 20 is represented by the distance Y (FIG. 2).

The portion of the receptor wall between the points 26 and 28 is of uniform thickness, and is quite thin, being less thick than any other portions of the wall in the receptor 12.

The wall thickness of the transition area 27 and the flared skirt wall 20 between the points 26 and 28 is preferably less than ½ of the thickness of the annular rim 30, and approximately 15-25% less thick than the tube wall 22.

In a typical construction for the breast receptor 12 having an overall length of 4.875 inches, the tubular wall thickness of the tube 22 is 0.094 inches, increasing to 0.104 inches in the transitional area 25 and then substantially reducing in thickness by 0.027 inches to a thickness of 0.077 inches at the terminal end portion 26. The wall thickness between the points 26 and 28 remains substantially uniform at 0.077 inches. Then the wall thickness gradually increases from the point 28 to an annular rim thickness of 0.1875 inches. In this particular receptor 12, the outer diameter of the annular rim 30 is 3.530 inches and the skirt is substantially frusto-conical having a flare angle of approximately 45° to the longitudinal axis L (FIG. 2).

In the above example, the distance X is approximately 1.504 inches and the distance Y is 0.570 inches. Moreover, the distance Z, from the annular rim 30 to the point 31 between the lower end of the stem 21 and the transition area 25 is 2.049 inches.

The gradual reduction in the wall thickness of the stem 21 toward the outer end of the receptor 12 provides the necessary flexibility to permit the upper or outer end portion of the stem 21 to more easily collapse on the side walls of the nipple 24, including the areola, as the pump bulb 13 is actuated to increase the vacuum within the stem 21. The reduced thickness of the transitional wall area 27 also permits the collapse of this thinner wall area against the areola and the adjoining surface of the breast B when received in lactating position within the receptor 12, as illustrated in FIG. 1.

Furthermore, the reduction in thickness of the receptor wall between the points 26 and 28 permit the fingers F of the mother to more readily squeeze or collapse these thin wall portions against the sides of the nipple 24 and the surrounding areola to produce a greater transfer of touch stimulus to these parts of the breast B.

The quality of the touch stimulus is critical for the release of the Human Prolactin Hormone (HPrl), which is necessary for the production of protein fat, sucrose, lactose and other nutrients by the milk production glands of the breast of a lactating woman. The nerve endings in the nipple and areola apparently have the ability to differentiate the quality of this touch stimulus, thus making the thinner wall between the points 26 and 28 all the more unique in this function.

The increase in wall thickness from the point 28 in the flared skirt wall 20 outwardly to the annular rim 30, which is the thickest portion of the receptor 12, provides a firmness and substantial rigidity in the rim 30 to engage the corresponding portion of the breast B and to establish the vacuum seal between the breast B and the interior of the receptor 12.

The breast receptor 12 is not only made of flexible material, but is preferably made of a material which can be readily autoclaved. The preferred form of material in the manufacture of the receptor 12 is thermo-setting silicone rubber. The material from which the receptor 12 is made, is preferably transparent, so that the operation of the receptor 12 and the flow of milk within the receptor may be easily observed.

The bulb pump 13 is a conventional bulb pump having a rear check valve 33 and a front check valve within the front portion 34 of the bulb 13. The bulb pump 13 functions in a conventional manner to create a vacuum within the suction line 15 when the bulb 13 is squeezed to position 13' and relaxed, in a conventional manner.

Any type control valve may be used, such as control valve member 14 disclosed in FIG. 1 and described in the co-pending application of Herbert H. Stuart et al, Ser. No. 437,347, in order to regulate the negative air pressure within the line 15, and ultimately within the receptor 12.

The coupling device 16 may include a disc-shaped connector 42 of slightly lesser diameter than the internal diameter of the cap 18, so that the connector 42 may loosely fit within the cap 18. A pair of tubules 43 and 44, preferably of equal length and size, extend entirely through the connector 42 and are spaced sufficiently close to each other that their outer ends will extend through the opening 45 existing in the conventional bottle cap 18.

The tubules 43 and 44 extend through the connector 42 and are preferably an integral part of the connector 42. The inner ends of the tubules 43 and 44 depend below the plane of the connector 42 a sufficient distance to prevent capillary action when liquid, such as milk, passes from the receptor tube 22 downward through the tubule 43 and into the milk bottle 17.

The major portions of the tubules 43 and 44 project from the upper side or plane of the connector 42, so that the outer end portions of the tubules 43 and 44 are telescopingly inserted into the open ends of the respective receptor tube 22 and suction conduit 15 with a tight sealing fit. The interior of the milk bottle 17 will then be in fluid communication with the breast receptor 12 and the suction line 15, which, in turn, is in fluid communication with the control valve 14 and the bulb 13.

In the operation of the breast pump 10, all of the parts are, of course, sterilized or autoclaved, and fitted together to be assembled as disclosed in FIGS. 1 and 2.

The breast pump 10 does not require any professional operator, so that the nursing or lactating mother alone, may handle the operation of the breast pump 10. The skirt 20 is placed over the breast B in a snug fitting relationship with the nipple 24 extending into the stem 21. The skirt 20 may be held in initially snug sealing relationship against the breast B by the fingers F of the mother, while the other hand, not shown, may be used to periodically pump or squeeze the bulb 13.

The flexibility of the thin wall portions of the skirt 20 and stem 21, permit periodic suction within the receptor 12 to contract and expand about the breast B, thereby massaging the breast B and particularly the nipple 24 and the areola, to express milk into the stem 21 and through the receptor tube 22 into the bottle 17.

The reduced pressure in the suction line 15 not only is transritted into the receptor 12 through the bottle 17, tube 22, and stem 21, but is also effective in drawing the expressed milk through the stem 21 and into the bottle 17.

The bulb 13 is preferably pumped at the normal sucking frequency of an infant at 70-120 strokes per minute, and the pressure within the breast receptor 12 is reduced to the mean pressure of a suckling infant, which is $-50$ to $-150$ millimeters of mercury, with a maximum suction of $-220$ millimeters of mercury.

The natural flexibility of the silicone material in the wall of the receptor 12 provides an opposite pull to the action of the bulb pump 13.

The expressing or lactating action is assisted by the mother's fingers F squeezing and relaxing the thin wall area of the skirt 20 and the transition area 27 about her own breast B. Although such manipulation is optional, nevertheless, it is recommended in conjunction, and in synchronism with the squeezing and relaxing of the bulb pump 13, in order to substantially duplicate the suckling action of a nursing infant.

It is further recommended for successful operation of the breast pump 10, to pre-moisten the interior silicone surface of the transition area 27 and the skirt wall 20 as well as the portion of the breast coming in contact with the thin wall area of the receptor 12, to further simulate or mimic the motion of the tissue of the breast B when being suckled by a nursing infant.

What is claimed is:

1. In a breast pump for the human breast having means for creating a vacuum, a breast receptor comprising:

(a) a skirt having a single frusto-conical wall of flexible material and a longitudinal axis, and terminating in a large open annular rim for receiving in substantially flush engagement a human breast in a lactating position, and having a small open end portion opposite said large open end, said smaller open end portion being larger than the nipple of the said human breast so that the nipple extends through said smaller end portion in said lactating position, (b) the angle of the frusto-conical wall with respect to said longitudinal axis of said skirt being approximately 40-50 deg., (c) an elongated hollow stem having a tubular wall, a longitudinal axis, and first and second opposite end portions, (d) the skirt wall of said smaller open end portion merging with the stem wall of said first open end portion to define an axially continuous transition portion means, said first open end portion being large enough to receive the nipple of the breast extending through said transition portion means in said lactating position, (e) said transition portion means extending from said first open end portion of said hollow stem and flaring toward said annular rim to occupy a substantial portion of said skirt wall, the axial length of said transition portion means being greater than midway between the smaller end portion of said transition portion means and said annular rim, (f) an elongated receptor tube having a tubular wall of substantially uniform thickness having one end merging with the stem wall of said second end portion, and having an opposite open end adapted to be connected in fluid communication with the means for creating a vacuum, (g) the thickness of said stem wall decreasing from its second end portion toward its first end portion, (h) the thickness of said annular rim being great enough to engage and establish a vacuum seal against the corresponding portion of the breast in said lactating position, (i) the thickness of the wall of said transition portion means being substantially less than the thickness of said annular rim to facilitate collapsing of said transition portion means upon the sides of the nipple and the areola received within and engaging the interior surface of said transition portion means in said lactating position, (j) said single frusto-conical skirt wall having an outer surface freely exposed to the grasp of a human operator for squeezing and relaxing said transition portion means, (k) the thickness of said transition portion means being sufficiently reduced to permit the optimum transfer of human touch stimulus by finger squeezing the exterior of said transition portion means and sufficiently flexible to contract and expand in response to the varying air pressures within said receptor against the sides of the nipple and the areola in said lactating position, to cause the release of the Human Prolactin Hormone, and (l) the thickness of the wall of said receptor tube being sufficient to prevent said wall from collapsing when the air pressure within said receptor tube is reduced under normal pumping action by the means for creating a vacuum.

2. The invention according to claim 1 in which the thickness of the transition portion means is substantially less than the thickness of the wall of said receptor tube.

3. The invention according to claim 1 in which the thickness of the wall of said transition portion means is substantially uniform.

4. The invention according to claim 1 in which the thickness of the wall of said transition portion means is less than one-half the thickness of said annular rim.

5. The invention according to claim 1 in which said angle is approximately 45 deg.

6. The invention according to claim 1 further comprising means for creating a vacuum including a vacuum pump and a control valve member in fluid communication with said opposite open end of said receptor tube.

7. The invention according to claim 1 in which said skirt, said stem and said receptor tube are integral and made of material which may be autoclaved.

8. The invention according to claim 7 in which said material is transparent.

9. The invention according to claim 7 in which said material is thermal-setting silicone rubber.

* * * * *